Figure 1:
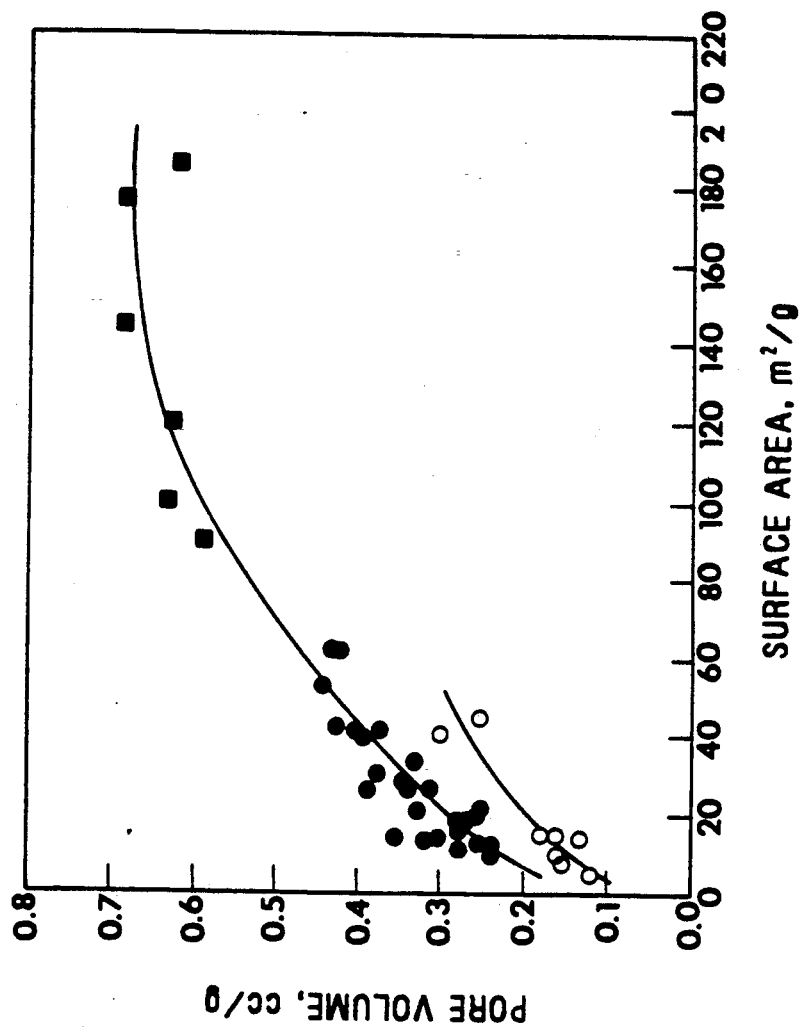

United States Patent [19]

Mauldin et al.

[11] Patent Number: 5,140,050
[45] Date of Patent: Aug. 18, 1992

[54] TITANIA CATALYSTS, THEIR PREPARATION, AND USE IN FISCHER-TROPSCH SYNTHESIS

[75] Inventors: Charles H. Mauldin; Kenneth L. Riley, both of Baton Rouge, La.

[73] Assignee: Exxon Research and Engineering Co., Florham Park, N.J.

[21] Appl. No.: 721,804

[22] Filed: Jun. 26, 1991

Related U.S. Application Data

[60] Continuation of Ser. No. 510,645, Apr. 18, 1990, abandoned, which is a division of Ser. No. 275,252, Nov. 23, 1988, Pat. No. 4,992,406.

[51] Int. Cl.$^5$ .................................................. C07C 1/04
[52] U.S. Cl. .................................................... 518/715
[58] Field of Search ........................................ 518/715

[56] References Cited

U.S. PATENT DOCUMENTS

| | | | |
|---|---|---|---|
| 4,042,614 | 8/1977 | Vannice et al. | 518/715 |
| 4,042,615 | 8/1977 | Vannice et al. | 518/715 |
| 4,568,663 | 2/1986 | Mauldin | 518/715 |
| 4,624,942 | 11/1986 | Dyer et al. | 518/717 |
| 4,663,305 | 5/1987 | Mauldin et al. | 518/715 |

*Primary Examiner*—Howard T. Mars
*Attorney, Agent, or Firm*—Jay Simon

[57] ABSTRACT

A process for the preparation of novel binder-containing titania supports, and catalyst compositions of improved porosity prepared from such supports, useful for Fischer-Tropsch synthesis. The supports are prepared by incorporating a small amount of an inorganic metal oxide binder, constituted of alumina, zirconia or silica, with titania. The catalysts are prepared by dispersing a catalytically effective amount of a metal, or metals, preferably cobalt, or cobalt plus an additional metal, or metals catalytically active in a Fischer-Tropsch reaction on the titania binder support.

7 Claims, 3 Drawing Sheets

TITANIA CATALYSTS, THEIR PREPARATION, AND USE IN FISCHER-TROPSCH SYNTHESIS

This is a continuation of application Ser. No. 510,645, filed Apr. 18, 1990 now abandoned which is a divisional of Ser. No. 275,252 now U.S. Pat. No. 4,992,406 filed Nov. 23, 1988.

FIELD OF THE INVENTION

This invention relates to improvements in a Fischer-Tropsch process, and Fischer-Tropsch catalysts. In particular, it relates to improved cobalt catalysts, process for the production of said catalysts, and process for the use of said catalysts in Fischer-Tropsch synthesis to produce liquid hydrocarbons, especially $C_{10}^+$ distillate fuels and other valuable products.

BACKGROUND OF THE INVENTION

Fischer-Tropsch synthesis, a process for the production of hydrocarbons from carbon monoxide and hydrogen, or synthesis gas, is well documented in the technical and patent literature. Fischer-Tropsch processes have also been commercially used, and are in operation today in some parts of the world.

The earlier Fischer-Tropsch catalysts were constituted for the most part of non-noble metals dispersed throughout a porous inorganic oxide support. The Group VIII non-noble metals, iron, cobalt, and nickel have been widely used in Fischer-Tropsch reactions, and these metals have been promoted with various other metals, and supported in various ways on various substrates, principally alumina. Most commercial experience, however, has been based on cobalt and iron catalysts. The first commercial Fischer-Tropsch operation utilized a cobalt catalyst, though later more active iron catalysts were also commercialized. The cobalt and iron catalysts were formed by compositing the metal throughout an inorganic oxide support. An important advance in Fischer-Tropsch catalysts occurred with the use of nickel-thoria on kieselguhr in the early thirties. This catalyst was followed within a year by the corresponding cobalt catalyst, 100 Co:18 ThO$_2$:100 kieselguhr, parts by weight, and over the next few years by catalysts constituted of 100 Co:18 ThO$_2$:200 kieselguhr and 100 Co:5 ThO$_2$:8 MgO:200 kieselguhr, respectively. These early cobalt catalysts, however, are of generally low activity necessitating a multiple staged process, as well as low synthesis gas throughout. The iron catalysts, on the other hand, are not really suitable for natural gas conversion due to the high degree of water gas shift activity possessed by iron catalysts. Thus, more of the synthesis gas is converted to carbon dioxide in accordance with the equation:

$H_2 + 2CO (CH_2)_x + CO_2;$ with too little of the synthesis gas being converted to hydrocarbons and water as in the more desirable reaction, represented by the equation:

$2H_2 + CO (CH_2)_x + H_2O.$

Considerable effort has been expended in recent years to improve cobalt catalysts. For example, U.S. Pat. No. 4,542,122 by Payne et al, which issued Sep. 17, 1985, describes improved cobalt catalyst compositions useful for the preparation of liquid hydrocarbons from synthesis gas. These catalyst compositions are characterized, in particular, as cobalt-titania or thoria promoted cobalt-titania, wherein cobalt, or cobalt and thoria, is composited or dispersed upon titania, or titania-containing support, especially a high rutile content titania. U.S. Pat. No. 4,568,663 by Mauldin, which issued Feb. 4, 1986, also discloses cobalt-titania catalysts to which rhenium is added to improve catalyst activity, and regeneration stability. These catalysts have performed admirably well in conducting Fischer-Tropsch reactions, and in contrast to earlier cobalt catalysts provide high liquid hydrocarbon selectivities, with relatively low methane formation.

These and other recently developed forms of cobalt-titania catalysts offer promise of a viable modern day large scale commercial Fischer-Tropsch plant which may utilize such catalyst, particularly catalysts formed by dispersion in one form or another of Co-Re, Co-Hf and Co-Ce on a rutile form of titania. Despite the admirably high activity and selectivity of these catalysts, however, there nonetheless remains a need for further improvements in the activity, selectivity and productivity of Fischer-Tropsch catalysts, notably cobalt catalysts. Productivity, which is defined as the standard volumes of carbon monoxide converted/volume catalyst/hour, is, of course, the life blood of a commercial operation. High productivities are essential in achieving commercially viable operations. However, it is also essential that high productivities be achieved without high methane formation, for methane production results in lower production of liquid hydrocarbons.

OBJECTS

It is accordingly, a primary object of this invention to provide further improved, novel titania supports, and supported catalyst compositions.

In particular, it is an object of this invention to provide novel titania supports and titania supported catalyst compositions, a process for the preparation of said catalyst compositions, and process utilizing said catalyst compositions for the conversion of synthesis gas at high productivities, with low methane formation, to high quality distillate fuels, particularly $C_{10}^+$ linear paraffins and olefins.

A particular object of this invention is to provide titania supports and titania supported cobalt catalyst compositions of improved porosity which, when dispersed in a reactor bed and used in a hydrocarbon synthesis reaction, produce a minimum pressure drop across the reactor; and catalysts of such character which possess good physical strength.

A further object is to provide a process utilizing such catalyst compositions for the production from synthesis gas of $C_{10}^+$ linear paraffins and olefins, at high productivity with decreased methane selectivity.

It is also an object to provide a process for the preparation of such supports and catalysts.

THE INVENTION

These objects and others are achieved in accordance with this invention embodying a novel binder-containing titania support, a particulate catalyst formed by dispersing a catalytically effective amount of a metal catalytically active in conducting a Fischer-Tropsch reaction upon said support, and the use of said catalyst in a Fischer-Tropsch reaction. A catalytically active metal, preferably cobalt, is dispersed upon a particulate titania, especially titania having a rutile:anatase ratio of at least about 3:2, within which there is dispersed a metal oxide binder selected from the group consisting of alumina, zirconia and silica, in that order of preference, in concentration ranging from about 0.1 percent to about 20 percent, preferably from about 0.5 percent to about 10 percent, and more preferably from about 1 percent to about 5 percent based on the weight of the total support. The incorporation into the titania of these small amounts of the binders, particularly in the lower concentrations, produce significantly better dispersion of the catalytically effective metal, notably cobalt, upon the support surfaces, higher activity, better selectivity and higher productivity than catalysts otherwise similar except that the metal oxide binder is not present within the titania support component of the catalyst. The metal can be substantially uniformly distributed throughout the titania-binder support component of the catalyst from the center of a particle outwardly, or preferably as a thin catalytically active layer, or film upon the peripheral outer surface of the titania-binder support. These catalyts can be used to produce, by contact and reaction at reaction conditions with an admixture of carbon monoxide and hydrogen, a distillate fuel constituted principally of an admixture of linear paraffins and olefins, particularly a $C_{10}^+$ distillate, at high productivity with low methane selectivity. This product can be further refined and upgraded to high quality fuels, and other products such as mogas, diesel fuel and jet fuel, especially premium middle distillate fuels of carbon numbers ranging from about $C_{10}$ to about $C_{20}$.

The titania-binder support particles are formed by incorporating, admixing or otherwise adding the required amount of alumina, zirconia or silica binder to the titania. The presence of the inorganic binder in the quantities expressed, particularly in the lower concentration, increases the porosity of the titania without eliminating the beneficial effects of the titania in conducting a Fischer-Tropsch reaction. The titania-binder support, after a metal is dispersed thereon, continues to behave in the Fischer-Tropsch reaction essentially as titania, but the Fischer-Tropsch reactions now occur within a more porous support as a consequence of which the activity and selectivity, and particularly the productivity, is increased vis-a-vis a catalyst otherwise similar reacted with a similar feed at similar conditions except that the titania base does not include the binder. It is found, that the greater benefits are obtained by the use of a binder in amount which does not exceed about 10 percent, and preferably in amount which does not exceed about 5 percent, based on the total weight of the titania-binder support particles. Whereas the binder can be used in concentration higher than about 10 percent, even as high as about 20 percent, generally no advantage is obtained by the use of the binder in these high concentrations; and higher concentrations of the binder can be detrimental.

Titania has long been studied by researchers as a support for use in catalysts, but the possibility of its large scale commercial use as a component of a catalyst useful in Fischer-Tropsch synthesis has only recently emerged with the discovery of the high activity and selectivity of cobalt-titania catalysts, where the titania support component is present in rutile form. The present discovery further enhances the potential of this catalyst, and others and of titania for this use. The catalyst, formed by the dispersion of a metal, notably cobalt, or cobalt and another metal or metals, as promoters or modifiers, e.g., rhenium, hafnium, cerium, on the titania-binder support, if the binder component is present in sufficiently low concentrations, continues not only to provide the normal advantages of the titania support component, but more—viz. higher activity and selectivity as well as higher productivity with lower methane production. The titania-binder support component, if the binder component is present in sufficiently low concentrations, thus continues to exhibit the behavior of titania; but a titania of greater porosity. Moreover, despite the greater porosity, and the advantages thereof, the catalyst possesses good physical strength. It has been found that the porosity of the titania, which typically has a pore volume (Hg) below 0.2 cc/g, can be increased above 0.2 cc/g, preferably from about 0.2 cc/g to about 0.5 cc/g, more preferably from about 0.25 cc/g to about 0.35 cc/g, by addition of the binder in the amounts recited to provide a surface area ranging from about 8 $m^2/g$ to about 70 $m^2/g$, preferably from about 10 $m^2/g$ to about 30 $m^2/g$. These advantages are obtained, it is believed, because significantly better dispersion of the metal, or metals, upon the higher porosity support is attained, which in turn produces increased hydrocarbon synthesis activity, selectivity and productivity.

A titania-alumina support is preferred. A "fumed" titania constituted of very small micron sized particles prepared by the oxidation of titanium tetrachloride, and alumina binder prepared by the hydrolysis of aluminum sec-butoxide are preferred materials for the preparation of the titania-alumina support particles. In the preparation of the titania-alumina support particles, via a preferred method of making these particles, the titania is mixed with the alumina binder in the desired proportions, water, and preferably a lubricant, suitably methyl cellulose or a polyglycol, and then extruded. It has been found that the titania crystallite size and particle size are particularly important for achieving satisfactory extrudability. (Crystallinity refers to the smallest individual particles of the titania consisting of an ordered arrangement of the titanium and oxygen atoms.) It is particularly desirable for good extrudability that the crystallite size of the titania used in the extrusion admixture be of average crystallite size below about 1000 Angstrom Units, preferably of average crystallite size ranging from about 200 Angstrom Units to about 600 Angstrom Units, as determined by measuring the line-width of the major anatase or rutile peak in the X-ray diffraction pattern, and that the average particle size of the titania be no greater than about 10 microns, preferably between about 0.5 microns and 5 microns, e.g., as measured by a commercially available instrument, suitably a Microtrac Analyzer. The extrusion per se is conducted in conventional manner at low torque to produce "green" extrudates of virtually any desired cross-section. Suitably, e.g., the extrudates are in the form of 1/20 inch diameter trilobates, or 1/32 inch diameter cylinders. In carrying out the extrusion, if the average crystallite size of the titania is too large, or the average particle size is too great, the titania-alumina mixture will be difficult to extrude, and the extrudates will lack the proper strength necessary for a catalyst support. (In contrast, alumina of 5 micron to 75 micron average particle size can be readily extruded without significant change in its extrudability characteristics when the titania is not present.) Virtually any type of extruder can be used in forming the extrudates, since neither the type of extruder or the form of the extrudate will significantly affect the porosity or surface area of the shaped titania-binder support. The green extrudates can be dried, typically by heating to temperatures ranging from about 90° C. to about 150° C., preferably at temperatures ranging from about 110° C. to about 120° C., and then calcined by heating to temperatures above about 400° C., preferably by heating to temperatures ranging from about 500° C. to about 850° C. Surface area decreases during calcination as anatase is transformed to rutile, and hence it is desirable to minimize the temperature and period of calcination to precisely those conditions which give the desired rutile content.

The catalytically active metal, or metals, preferably cobalt or cobalt promoted or modified with an additional metal, or metals, can be dispersed upon the calcined titania-binder support particles in a manner which will distribute the metal, or metals, essentially uniformly throughout the particles from the center outwardly, or essentially upon the peripheral surface of the particle, preferably the latter. For example, catalysts can be prepared from the calcined titania-binder support particles by techniques known in the art for the preparation of other catalysts. In distributing the metal, or metals, uniformly throughout the calcined titania-binder support particles, e.g., the metal, or metals, can be deposited on the support particles from solution in preselected amounts to provide the desired absolute amounts, and weight ratio of the respective metal, or metals. Suitably, e.g., cobalt, or cobalt and rhenium, are composited with support by contacting the support with a solution of a cobalt-containing compound, or salt, or a rhenium-containing compound, or salt, followed by impregnation of the other component. Optionally, the cobalt, or cobalt and rhenium can be co-impregnated upon the support. The cobalt used in the impregnation can be any organometallic or inorganic compound which decomposes to give cobalt oxides upon calcination, such as cobalt nitrate, acetate, acetylacetonate, naphthenate, carbonyl, or the like. Likewise the rhenium compound used in the impregnation can be any organometallic or inorganic compound which decomposes to give rhenium oxides upon calcination, e.g., perrhenic acid, ammonium perrhenate and the like. The amount of impregnation solution used should be sufficient to completely immerse the carrier, usually within the range from about 1 to 20 times of the carrier by volume, depending on the metal, or metals, concentration in the impregnation solution. The impregnation treatment can be carried out under a wide range of conditions including ambient or elevated temperatures. On the other hand, the catalytically active cobalt component is most preferably dispersed and supported upon the peripheral surface of the calcined titania-binder particles as a thin catalytically active surface layer, or film, ranging in average thickness from about 20 microns to about 250 microns, preferably from about 40 microns to about 150 microns, with the loading of the cobalt expressed as the weight metallic cobalt per packed bulk volume of catalyst ranging from about 0.01 grams (g) per cubic centimeter (cc) to about 0.15 g/cc, preferably from about 0.03 g/cc to about 0.09 g/cc catalyst. The feature of a high cobalt metal loading in a thin catalytically active layer located at the surface of the particles can optimize the activity, selectivity and productivity of the catalyst in producing liquid hydrocarbons from synthesis gas, while minimizing methane formation.

The surface impregnated catalysts can be prepared by spray techniques where a dilute solution of a cobalt compound, alone or in admixture with a promoter metal compound, or compounds, as a spray is repetitively contacted with hot titania-binder support particles. The particulate support particles are maintained at temperatures equal to or above about 140° C. when contacted with the spray, and suitably the temperature of the titania-binder support particles ranges from about 140° C. up to the decomposition temperature of the cobalt compound, or compounds in admixture therewith; preferably from about 140° C. to about 190° C. The cobalt compound employed in the solution can be any organometallic or inorganic compound which decomposes to give cobalt oxide upon initial contact or upon calcination, such as cobalt nitrate, cobalt acetate, cobalt acetylacetonate, cobalt naphthenate, cobalt carbonyl, or the like. Cobalt nitrate is especially preferred while cobalt halide and sulfate salts should generally be avoided. The cobalt salts may be dissolved in a suitable solvent, e.g., water, organic or hydrocarbon solvent such as acetone, methanol, pentane or the like. The total amount of solution used should be sufficient to supply the proper catalyst loading, with the film being built up by repetitive contacts between the support and the solvent. The preferred catalyst is one which consists essentially of cobalt, or cobalt and promoter, dispersed upon the titania-binder support, especially a support the titania portion of which is comprised of rutile. Suitably, the hot titania-binder support particles are contacted with a spray which contains from about 0.05 g/ml to about 0.25 g/ml, preferably from about 0.10 g/ml to about 0.20 g/ml, of the cobalt compound or cobalt compound plus the compound containing the promoter metal, generally from at least about 3 to about 12 contacts, preferably from about 5 to about 8 contacts, with intervening drying and calcination steps being required to form surface films of the required thicknesses. The hot titania-binder support particles, in other words, are spray-contacted in a first cycle which includes the spray contact per se with subsequent drying and calcination, a second cycle which includes per se with subsequent drying and calcination, etc. to form a film of the required thickness and composition. The drying steps are generally conducted at temperatures ranging above about 20° C., preferably from about 20° C. to about 125° C., and the calcination steps at temperatures ranging above about 150° C., preferably from about 150° C. to about 300° C.

Metals such as rhenium, zirconium, hafnium, cerium, thorium and uranium, or the compounds thereof, can be added to cobalt to increase the activity and regenerability of the catalyst. Thus, the catalysts which contain the cobalt metal uniformly dispersed throughout the support particles, or those wherein the cobalt is dispersed on the support particles as thin catalytically active layers, or films, can include in addition to a catalytically active amount of cobalt, any one or more of rhenium, zirconium, hafnium, cerium, uranium, and thorium, admixture thereof, or admixture of these with other metals or compounds thereof. Preferred catalytically active metals thus include cobalt-rhenium, cobalt-zirconium, cobalt-hafnium, cobalt-cerium, cobalt-uranium, and cobalt-thorium, with or without the additional presence of other metals or compounds thereof.

A particularly preferred catalyst is one wherein the cobalt, or the cobalt and a promoter, is dispersed upon the titania-binder support particles, the titania component of which has a rutile:anatase weight ratio of at least about 3:2, as determined by ASTM D 3720-78: Standard Test Method for *Ratio of Anatase to Rutile In Titanium*

*Dioxide Pigments By Use of X-Ray Diffraction.* Generally, the catalyst is one wherein the titania component thereof has a rutile:anatase ratio ranging at least about 3:2 to about 100:1, or greater, and more preferably from about 4:1 to about 100:1, or greater. Where any one of rhenium, zirconium, hafnium, cerium, thorium, or uranium metals, respectively, is added to the cobalt as a promoter, the metal is added to the cobalt in concentration sufficient to provide a weight ratio of cobalt:metal promoter ranging from about 30:1 to about 2:1, preferably from about 20:1 to about 5:1. Rhenium and hafnium are the preferred promoter metals, rhenium being more effective in promoting improved activity maintenance on an absolute basis, with hafnium being more effective on a cost-effectiveness basis. These catalyst compositions, it has been found, produce at high productivity, with low methane selectivity, a product which is predominately $C_{10}^+$ linear paraffins and olefins, with very little oxygenates. These catalysts also provide high activity, high selectivity and high activity maintenance in the conversion of carbon monoxide and hydrogen to distillate fuels.

In conducting synthesis gas reactions the total pressure upon the CO and $H_2$ reaction mixture is generally maintained above about 80 psig, and preferably above about 140 psig. It is generally desirable to employ carbon monoxide, and hydrogen, in molar ratio of $H_2$:CO above about 0.5:1 and preferably equal to or above about 1.7:1 to increase the concentration of $C_{10}^+$ hydrocarbons in the product. Suitably, the $H_2$:CO molar ratio ranges from about 0.5:1 to about 4:1, and preferably the carbon monoxide and hydrogen are employed in molar ratio $H_2$:CO ranging from about 1.7:1 to about 2.5:1. In general, the reaction is carried out at gas hourly space velocities ranging from about 100 V/Hr/V to about 5000 V/Hr/V, preferably from about 300 V/Hr/V to about 1500 V/Hr/V, measured as standard volumes of the gaseous mixture of carbon monoxide and hydrogen (0° C., 1 Atm.) per hour per volume of catalyst. The reaction is conducted at temperatures ranging from about 160° C. to about 290° C., preferably from about 190° C. to about 260° C. Pressures preferably range from about 80 psig to about 600 psig, more preferably from about 140 psig to about 400 psig. The product generally and preferably contains 60 percent, or greater, and more preferably 75 percent, or greater, $C_{10}^+$ liquid hydrocarbons which boil above 160° C. (320° F.).

The invention will be more fully understood by reference to the following examples and demonstrations which present comparative data illustrating its more salient features.

In the first set of runs which follow there is described a series of preparations wherein titania, and alumina, silica, and zirconia, respectively, are mixed together to form titania-binder support particles, the binder in concentration ranging from 1 through 21 percent, and greater, with the titania constituting the balance of the titania-binder support particles, based on the weight of the support particles. Comparisons of pore volume and surface area of the different titania-binder compositions of different shape are made with titania support particles which contain no binder.

EXAMPLE 1

In a first series of preparations, titania was admixed with an alumina, silica, or zirconia binder. The alumina binder was made by the hydrolysis of $Al(OC_4H_9)_3$, or a titania-alumina composite made by the co-hydrolysis of $Al(OC_4H_9)_3$ and $Ti(OC_3H_7)_4$. The titania was purchased directly from a commercial source. The titania was mull-mixed with the alumina binder, water, and a lubricant—methocel or polyglycol. The admixture, where extrudates were formed, was extruded via the use of a low torque 0.8 inch Welding Engineer's extruder, or a Carver Press extruder, as 1/20 inch diameter trilobes (TRIL) or 1/32 inch diameter cylinders (1/32), dried at 120° C., and then calcined at 500° C. to 850° C.

The individual preparations are described by reference to Table 1, Support Nos. 1–8 (and 47) describing pure titania, in both extrudate and spherical forms, prepared without a binder as reference materials. Support Nos. 9–14 (and 43–46) of Table 1 are extrudates containing, except in three instances, more binder than titania, including some of the examples of pure alumina extrudates. Support Nos. 15–41 exemplify the supports of this invention, these supports illustrating the effect of binder content in differing concentrations. Support Nos. 15–22, in particular, illustrate the effect of alumina binder content using the trilobate form, calcined at 650° C. The more alumina added, the higher the pore volume and surface area that is produced. Support Nos. 23–29 show the effect of calcination on a preferred composition, viz. 96.5% $TiO_2$/3.5% $Al_2O_3$. Support Nos. 30–33 show that steaming is equivalent to calcination; both converting anatase to rutile and leading to a reduction in surface area. Pore volume also decreases while the medium pore diameter increases. A wide variety of alumina containing materials are demonstrated to be useful as a binder. Pure alumina gels and titania-alumina cogels made by alkoxide hydrolysis are satisfactory as are a number of different commercially available aluminas. Support Nos. 37–41 show that silica and zirconia also function as binders, and that alternate source of titania are suitable starting materials.

Reference is made to the following "Legend For Table Headings" and to Table 1. The legend provides background information for Table 1.

| LEGEND FOR TABLE HEADINGS | | |
|---|---|---|
| Heading | Designations | Description, Or Source |
| $TiO_2$ Source | Company A | $TiO_2$, 35% rutile |
| | ALKOX | $TiO_2$ from $Ti(OC_3H_7)_4$ hydrolysis |
| | CHLOR | $TiO_2$ from $Ti(Cl)_4$ neutralization with $NH_4OH$, 100% anatase |
| Extruder | CP-xxxx | Carver Press - psi pressure used |
| | WE-xx | Welding Engineers 0.8" extruder - % torque used |
| Size | SPHR | 1 mm spheres (made by Company B) |
| | TRIL | 1/20 inch trilobe extrudates made with 1-hole die |
| | 1/32 | 1/32 inch extrudates made with 3-hole die, 10 wt. % polyglycol added to mull-mix |
| Binder | $Al_2O_3$ | Made by hydrolysis of $Al(OC_4H_9)_3$ |
| | $Al_2O_3$—$TiO_2$ | Made by co-hydrolysis of $Al(OC_4H_9)_3$ and $Ti(OC_3H_7)_4$, composition by wt. |
| | C | Company C |
| | D | Company D |

-continued

LEGEND FOR TABLE HEADINGS

| Heading | Designations | Description, Or Source |
|---|---|---|
| | E | Company E |
| | $SiO_2$ | Company F |
| | $ZrO_2$ | Made by hydrolysis of $Zr(OC_3H_7)_4$ |
| % Binder | — | Corresponds to the % of $Al_2O_3$, $SiO_2$ or $ZrO_2$ added to the $TiO_2$ on a dry basis. |
| Hg PD | — | Median pore diameter measured by Hg porosimetry with a contact angle of 125° C. and surface tension of 485 dynes/cm |
| % Rutile | — | ASTM D 3720-78 | strated by the use of different symbols, the upper curve can be petitioned into materials containing greater than (black squares), or less than (black circles) about 20 percent binder. The latter show significantly higher pore volume at a given surface area than pure titania, or titania which contains no binder. The precise level of pore volume and surface area within the lower portion of this curve is obtained by varying the binder content between about 1 and 20% and final calcination temperature applied to the support. As the binder concentration increases, the pore volume and surface area increases. As calcination temperature is increased, the pore volume and surface area are decreased. Optimally, the amount of binder used should not exceed about 10 percent, and preferably should not exceed about 5 percent.

Catalysts of extrudate shape offer process advantages over other forms and, as earlier suggested, the crystal-

TABLE 1

| Support Number | $TiO_2$ Source | Extruder (P) | Size | Binder | % Binder in Extrud. | Hg PV, cc/g | Hg PD, Ang. | BET SA, $m^2/g$ | % Rutile in $TiO_2$ | Calc. Deg. C.-hr. |
|---|---|---|---|---|---|---|---|---|---|---|
| 1 | * | — | SPHR | NONE | 0.0 | 0.253 | 140 | 45 | 27 | — |
| 2 | * | — | SPHR | NONE | 0.0 | 0.162 | 270 | 15 | 92 | 700-1 |
| 3 | * | — | SPHR | NONE | 0.0 | 0.134 | 250 | 14 | 95 | 700-1 |
| 4 | * | — | SPHR | NONE | 0.0 | 0.120 | 481 | 5 | 100 | 840-1 |
| 5 | * | CP-1900 | TRIL | NONE | 0.0 | 0.154 | 389 | 8 | 98 | 650-16 |
| 6 | ALKOX | — | TRIL | NONE | 0.0 | 0.160 | | 10 | 94 | 650-50 |
| 7 | * | WE-35 | 1/32 | NONE | 0.0 | 0.299 | | 41 | | 500-16 |
| 8 | * | WE-35 | 1/32 | NONE | 0.0 | 0.180 | | 15 | | 600-16 |
| 9 | * | WE-35 | TRIL | $Al_2O_3$ | 60.0 | 0.588 | 141 | 91 | 27 | 650-50 |
| 10 | CO-GEL | WE-15 | TRIL | 30 $TiO_2$-70 $Al_2O_3$ | 70.0 | 0.620 | | 187 | 85 | 650-50 |
| 11 | CO-GEL | | TRIL | 30 $TiO_2$-70 $Al_2O_3$ | 70.0 | 0.632 | 147 | 121 | 93 | 800-3 |
| 12 | NONE | WE-30 | TRIL | $Al_2O_3$ | 100.0 | 0.684 | 106 | 178 | 0 | 650-50 |
| 13 | NONE | WE-30 | TRIL | $Al_2O_3$ | 100.0 | 0.685 | 125 | 146 | 0 | 800-3 |
| 14 | * | WE-20 | 1/32 | $SiO_2$ | 30.0 | 0.633 | 211 | 101 | 46 | 800-2 |
| 15 | * | CP-2000 | TRIL | 80 $TiO_2$-20 $Al_2O_3$ | 1.0 | 0.270 | | 17 | 96 | 650-50 |
| 16 | * | CP-1900 | TRIL | 61 $TiO_2$-39 $Al_2O_3$ | 2.0 | 0.280 | | 19 | 95 | 650-50 |
| 17 | * | WE-30 | TRIL | 35 $TiO_2$-65 $Al_2O_3$ | 3.3 | 0.372 | 265 | 42 | 27 | 650-50 |
| 18 | * | WE-15 | TRIL | 30 $TiO_2$-70 $Al_2O_3$ | 3.5 | 0.408 | 312 | 42 | 53 | 650-50 |
| 19 | * | CP-1900 | TRIL | $Al_2O_3$ | 5.0 | 0.430 | 426 | 34 | | 650-50 |
| 20 | * | WE-30 | TRIL | $Al_2O_3$ | 5.0 | 0.338 | 251 | 27 | 29 | 650-50 |
| 21 | * | WE-15 | TRIL | $Al_2O_3$ | 10.0 | 0.430 | 231 | 63 | 29 | 650-50 |
| 22 | * | WE-20 | TRIL | 30 $TiO_2$-70 $Al_2O_3$ | 21.0 | 0.420 | | 63 | 27 | 650-50 |
| 23 | * | WE-15 | TRIL | 30 $TiO_2$-70 $Al_2O_3$ | 3.5 | 0.387 | 454 | 27 | 82 | 750-3 |
| 24 | * | WE-15 | TRIL | 30 $TiO_2$-70 $Al_2O_3$ | 3.5 | 0.326 | 590 | 22 | 96 | 800-1 |
| 25 | * | WE-15 | TRIL | 30 $TiO_2$-70 $Al_2O_3$ | 3.5 | 0.354 | 678 | 15 | 98 | 800-3 |
| 26 | * | WE-15 | TRIL | 30 $TiO_2$-70 $Al_2O_3$ | 3.5 | 0.301 | 697 | 15 | 100 | 800-16 |
| 27 | * | WE-15 | TRIL | 30 $TiO_2$-70 $Al_2O_3$ | 3.5 | 0.276 | 590 | 12 | 100 | 850-3 |
| 28 | * | WE-15 | TRIL | 30 $TiO_2$-70 $Al_2O_3$ | 3.5 | 0.254 | 1151 | 13 | 100 | 850-10 |
| 29 | * | WE-15 | TRIL | 30 $TiO_2$-70 $Al_2O_3$ | 3.5 | 0.237 | 1706 | 10 | 100 | 850-72 |
| 30 | * | WE-15 | TRIL | $Al_2O_3$ | 10.0 | 0.424 | 305 | 43 | 33 | 600-50 |
| 31 | * | WE-15 | TRIL | $Al_2O_3$ | 10.0 | 0.441 | | 54 | 26 | 625-50 |
| 32 | * | WE-15 | TRIL | $Al_2O_3$ | 10.0 | 0.375 | | 31 | 68 | 750-3 |
| 33 | * | WE-15 | TRIL | $Al_2O_3$ | 10.0 | 0.343 | | 29 | 68 | 775-3 |
| 34 | * | WE-35 | 1/32 | $Al_2O_3$CoC | 3.5 | 0.266 | 455 | 19 | 96 | 800-3 |
| 35 | * | WE-25 | 1/32 | $Al_2O_3$CoD | 3.5 | 0.256 | 420 | 20 | 92 | 800-3 |
| 36 | * | WE-30 | 1/32 | $Al_2O_3$CoE | 3.5 | 0.277 | 516 | 16 | 99 | 800-3 |
| 37 | * | WE-30 | 1/32 | $SiO_2$ | 3.5 | 0.252 | 440 | 22 | 99 | 800-3 |
| 38 | * | WE-35 | 1/32 | $ZrO_2$ | 3.5 | 0.394 | 284 | 40 | | 500-16 |
| 39 | * | WE-35 | 1/32 | $ZrO_2$ | 3.5 | 0.311 | 317 | 27 | | 600-16 |
| 40 | ALKOX | WE-15 | 1/32 | $Al_2O_3$ | 3.5 | 0.240 | 690 | 10 | 74 | 800-3 |
| 41 | CHLOR | WE-8 | 1/32 | $Al_2O_3$ | 2.0 | 0.317 | 923 | 14 | 59 | 800-3 |
| 42 | * | WE-30 | 1/32 | Polyglycol | 0.0 | 0.188 | 293 | 16 | | 600-16 |
| 43 | * | WE-15 | TRIL | 30 $TiO_2$-70 $Al_2O_3$ | 3.5 | 0.298 | 612 | 25 | 97 | 800-3 |
| 44 | * | WE-30 | TRIL | $Al_2O_3$ | 5.0 | 0.209 | 576 | 4 | 100 | 800-3 |
| 45 | * | WE-15 | TRIL | $Al_2O_3$ | 10.0 | 0.265 | 400 | 22 | 87 | 800-3 |
| 46 | * | WE-20 | TRIL | 30 $TiO_2$-70 $Al_2O_3$ | 21.0 | 0.405 | 453 | 37 | 85 | 800-3 |
| 47 | * | — | SPHR | NONE | 0.0 | 0.113 | 270 | 17 | 86 | 700-1 |

* Company A

These data are graphically represented by reference to FIG. 1, a plot of pore volume (PV) measured by mercury porosimetry versus surface area (SA) by BET analysis. The data points fall into two distinct categories: (1) a lower curve (open circles) of pure titania supports, or titania supports with no binder, and (2) an upper curve of titania supports containing binders. As demonlite size and particle size of the titania must be carefully controlled for satisfactory extrusion, and to obtain satisfactory extrudates. The following example demonstrates the importance of the crystalline size and particle size of the titania.

EXAMPLE 2

The following Table 2 lists the results of a series of extrusion runs with a variety of titanias from different sources. The table gives the anatase and rutile compositions, crystallite sizes in Angstroms Units, average particle size diameters of the titanias in microns, and the extrudability characteristics of the titania in the preparation of 1/32 inch diameter extrudates by passage of the titanias through a 3-hole die in a 0.8 inch Welding Engineer's extruder.

TABLE 2

| Titania Source | Composition, Wt % Anatase | Composition, Wt % Rutile | Crystallite Size, A | Particle Size, u | Extrudability |
|---|---|---|---|---|---|
| Company A | 77 | 23 | 313/545 | 1.0 | Good |
| Calcined Company A | 0 | 100 | 930 | 7.3 | Poor |
| Company G | 0 | 100 | 6305 | 0.5 | Poor |
| Company H | 7 | 93 | 3409 | 0.6 | Poor |
| Company I | 8 | 92 | 5841 | 0.5 | Poor |
| Alkoxide Hydrolysis | 100 | 0 | <120 | 16.2 | Poor |
| $TiCl_4$ Neutraliz.[1] | 60 | 40 | <220/<220 | 8.7 | Poor |
| $TiCl_4$ Neutraliz.[2] | 100 | 0 | <200 | 23.9 | Poor |
| $TiCl_4$ Neutralized[2] Ball Milled | 100 | 0 | <220 | 4.7 | Fair |

[1] Aqueous $NH_4OH$ added to acqueous solution of $TiCl_4$.
[2] Aqueous solution of $TiCl_4$ added to $NH_4OH$.

It is clear that good performance is obtained only if the crystallite size is less than about 1000 Angstrom Units, preferably about 600 Angstrom Units, and the particle size is less than about 5 microns preferably less than about 2 microns. If either property exceeds these values the titania is difficult to extrude. Often, when such conditions are not met, the extruder plugs, and the extrudates that are produced are very weak.

EXAMPLE 3

This example demonstrates the use of the higher porosity titania-binder supports as catalysts for use in Fischer-Tropsch synthesis, i.e., the production of hydrocarbons from carbon monoxide and hydrogen. The data show that significantly better metal dispersion and higher hydrocarbon synthesis activity result when cobalt is dispersed on the more porous supports.

Table 3 lists the catalysts prepared from supports described in Table 1, each support being identified in Table 3 by number corresponding with that given in Table 1. Table 3 gives the composition of the catalyst prepared from the support, their performance in $O_2$ chemisorption and in a hydrocarbon synthesis run. The catalysts were prepared by impregnating the support with an acetone solution of cobalt nitrate and perrhenic acid on a rotary evaporator, drying in a vacuum oven at 140° C., and calcining in flowing air at 250° C. in an oven. Oxygen chemisorption was performed at 25° C. by measuring the uptake of oxygen pulses from a helium carrier gas stream, passed over samples of catalyst which were reduced in hydrogen for 16 hours at 450° C. The catalytic test was conducted in a unit using a small charge of catalyst diluted with an equal volume of titania. The catalyst was crushed and screened to 60-150 Tyler mesh size and reduced in hydrogen at 450° C. for 1 hour. Run conditions were 200° C., 280 psig, with a feed of 64% $H_2$/32% CO/4% Ne. Space velocities used for each example are shown in Table 3.

It is useful to express the catalytic data in terms of "volumetric productivity," which is calculated by multiplying the fraction CO converted times the space velocity times the fraction CO in the feed. Since reactor volume is an expensive item, high volumetric productivity is a very desirable property of the catalyst. For hydrocarbon synthesis over cobalt catalysts, in the absence of a diffusion limitation, productivity is a direct function of three factors: cobalt loading, cobalt dispersion, and cobalt oxidation state. It is desirable to maximize the loading and the dispersion while maintaining the cobalt in the zero-valent state, which is the only phase active in hydrocarbon synthesis. However, these factors often work against each other, so the best catalysts represent a compromise. These three factors are taken into account in defining this invention.

TABLE 3

| Support Number | Wt % Co | Wt % Re | Density g/cc | $O_2$ Chemis. O/Co | GHSV | % Co Conv. | Mol % $CH_4$ | TON |
|---|---|---|---|---|---|---|---|---|
| 42 | 5.78 | 0.47 | 1.45 | 0.256 | 1250 | 73 | 4.2 | 32.8 |
| 16 | 6.06 | 0.56 | 1.24 | 0.372 | 1250 | 85 | 4.9 | 29.3 |
| 39 | 5.47 | 0.37 | 1.13 | 0.342 | 1125 | 71 | 3.8 | 29.2 |
| 23 | 4.52 | 0.39 | 0.958 | 0.410 | 850 | 77 | 4.7 | 28.4 |
| 43 | 4.67 | 0.46 | 1.11 | 0.318 | 850 | 74 | 4.6 | 29.4 |
| 19 | 5.80 | 0.50 | 0.933 | 0.408 | 1000 | 81 | 4.3 | 28.3 |
| 20 | 5.85 | 0.50 | 1.00 | 0.344 | 1000 | 75 | 4.8 | 28.7 |
| 44 | 5.64 | 0.53 | 1.45 | 0.318 | 1250 | 76 | 4.5 | 28.2 |
| 21 | 5.34 | 0.44 | 0.858 | 0.367 | 750 | 72 | 5.5 | 24.8 |
| 45 | 5.55 | 0.49 | 1.18 | 0.418 | 1000 | 83 | 4.3 | 23.4 |
| 22 | 5.83 | 0.45 | 0.767 | 0.527 | 750 | 67 | 5.4 | 16.5 |
| 46 | 6.15 | 0.44 | 0.967 | 0.422 | 750 | 85 | 4.3 | 19.6 |
| 9 | 5.57 | 0.40 | 0.683 | 0.504 | 500 | 83 | 4.7 | 16.7 |
| 11 | 5.35 | 0.37 | 0.717 | 0.469 | 500 | 57 | 6.7 | 12.2 |
| 12 | 5.79 | 0.44 | 0.600 | 0.536 | 500 | 62 | 6.2 | 12.8 |
| 13 | 5.59 | 0.51 | 0.592 | 0.527 | 500 | 54 | 6.7 | 11.9 |
| 47 | 5.42 | 0.45 | 1.65 | 0.233 | 1000 | 75 | 4.8 | 27.8 |

Figure 2:
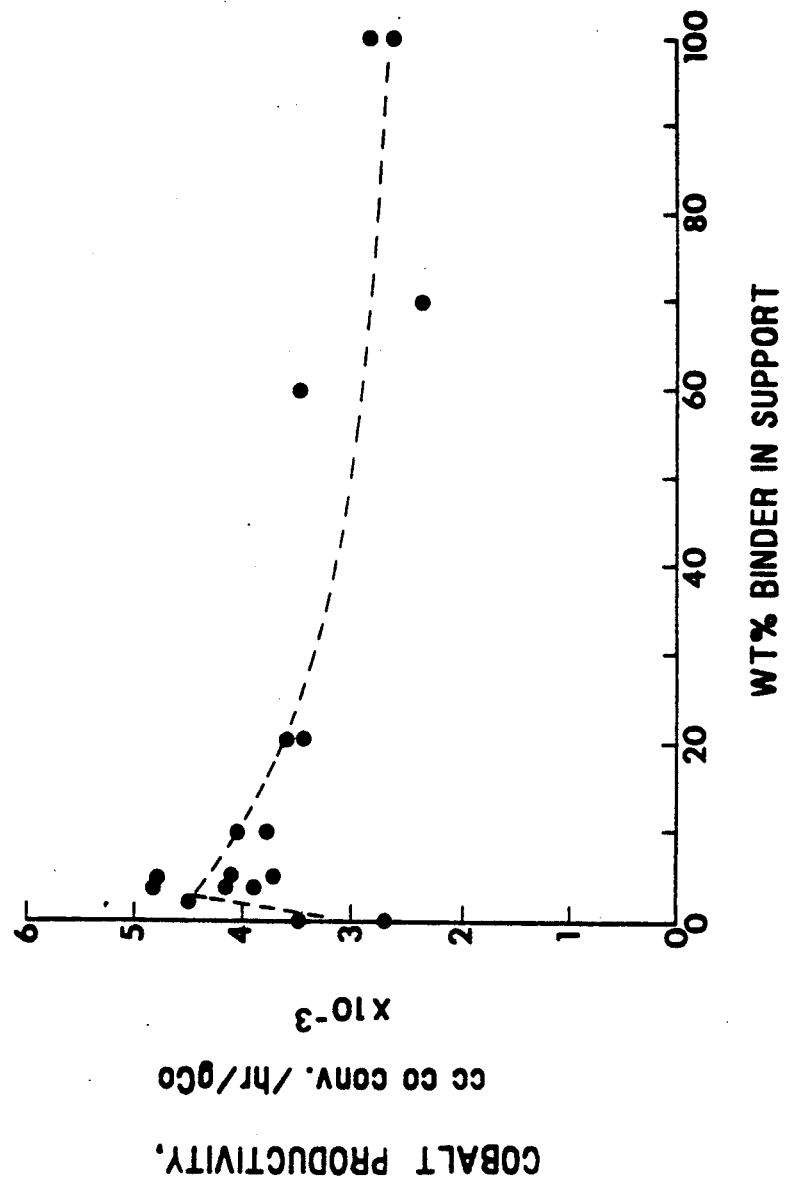

The runs made with these catalysts are summarized in FIG. 2 with a plot of "cobalt productivity" versus binder content in the support. Cobalt productivity is calculated by simply dividing the volumetric productivity by the volumetric cobalt loading. As FIG. 2 shows, cobalt productivity increases significantly upon the addition of a small amount of binder and then falls back down after more than about 20% binder. This activity credit is a key and novel feature of this invention.

The increase in activity upon the incorporation of a small amount of binder is attributed to an increase in cobalt dispersion. O₂ chemisorption analysis indicates that the ratio of O/Co, which is a measure of relative dispersion, correlates with the pore volume of the support. Thus, as the binder increases the pore volume of the support, dispersion increases on the catalyst. This trend actually continues out all the way to pure alumina. Hydrocarbon synthesis activity, however, does not continue to increase as binder is added. In fact, activity drops because the support is becoming too "alumina-like." Surface analysis by X-ray photoelectron spectroscopy indicates that cobalt oxide is only partially reduced on alumina, compared to titania where complete reduction occurs. Thus, too much binder gives high dispersion but this potential advantage is more than offset by the poor reducibility.

The differences between titania and alumina are illustrated quite clearly by converting the cobalt productivity values into a "turnover number" as follows:

$$TON = \frac{\text{Cobalt Productivity } (2.41 \times 10^{-3})}{\text{(O/Co ratio from O}_2\text{ chemisorption)}}$$

= Moles of CO converted per hour per mole of "O" sites

Figure 3:
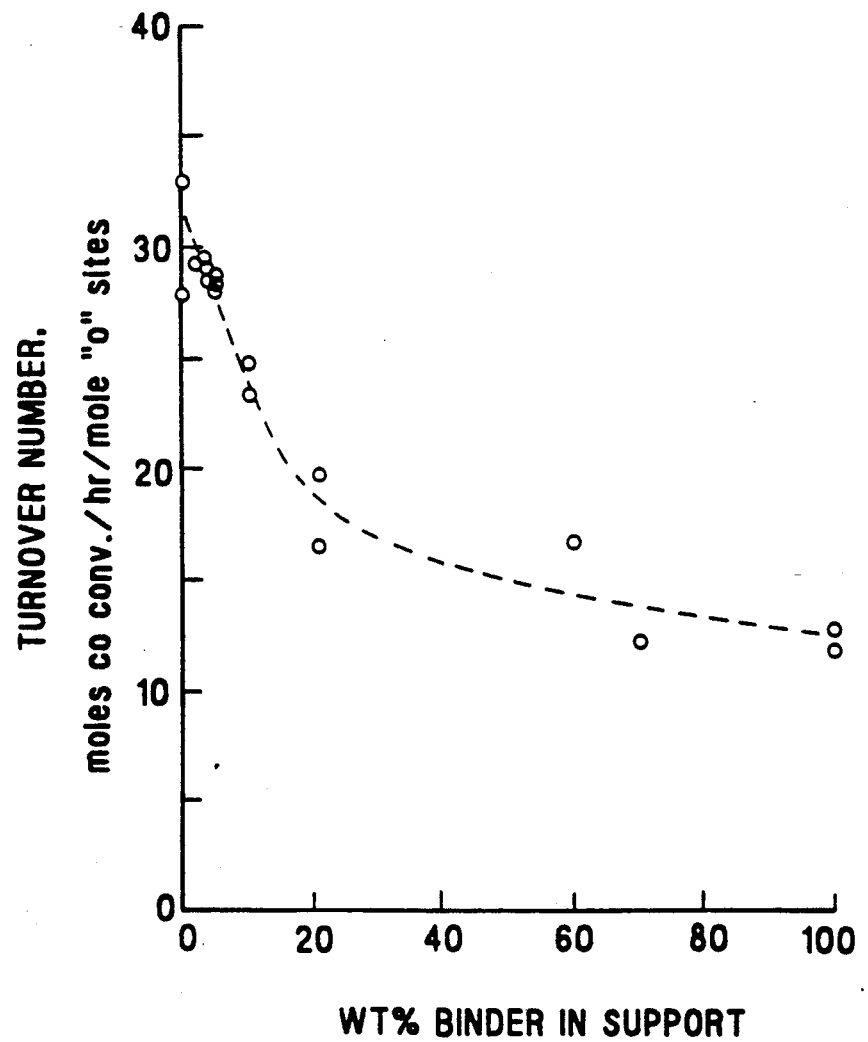
Figure 3:
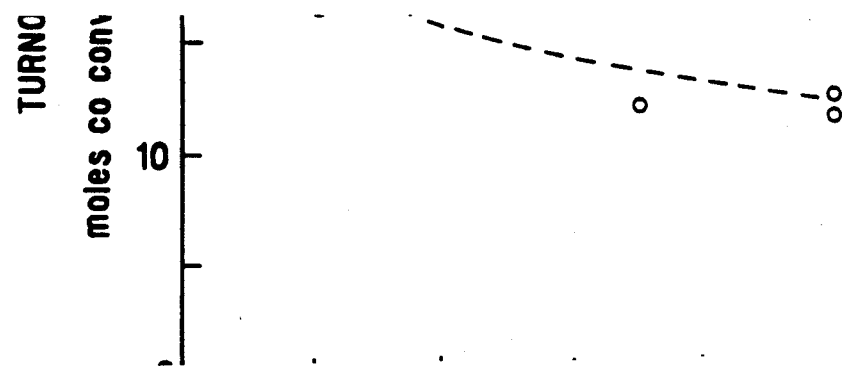

A plot of TON versus binder content, FIG. 3, shows the dramatic loss in "intrinsic" activity that accompanies the incorporation of a binder into the support. Less than 20%, preferably less than 10%, and most preferably less than 5% binder should be present in order to maintain the highest cobalt turnover number.

The proper amount of binder can thus increase the volumetric productivity of the catalyst in the absence of diffusion limitations. This is a significant result for all catalyst forms; including especially catalysts in powder form. However, the credits of the more porous support actually gain in importance when some diffusion limitation is encountered, as is the case with most fixed bed forms of the catalyst. Here the extra porosity aids the diffusion of the reactants, leading to an additional activity and important selectivity advantage. This feature of the invention is supported by fundamental diffusion theory, as discussed for example in Froment and Bischoff's CHEMICAL REACTOR ANALYSIS AND DESIGN, p. 167.

EXAMPLE 4

Runs 48 and 49, summarized in Table 4 are catalysts wherein the cobalt is coated on the surface of the support, these data illustrating the benefits of improved porosity under conditions of some diffusion limitation. The catalysts were made by repetitively spraying hot support particles with an aqueous solution of cobalt nitrate and perrhenic acid. The volumetric cobalt loadings and thicknesses of the surface metal coatings are essentially constant in this comparison. Thus, the productivity and selectivity credits of Run 49 vis-a-vis Run 48 may be attributed to the use of the more porous support, which contains 3.5% alumina as binder.

TABLE 4

| Run Number | 48 | 49 |
|---|---|---|
| Support Properties | | |
| Form | 1 mm sphere | 1/32 extrud |
| Wt. % binder (Al₂O₃) | 0 | 3.5 |
| Surface area, m²/g | 15 | 24 |
| Pore volume (Hg), cc/g | 0.162 | 0.251 |
| Porosity | 0.41 | 0.54 |
| Catalyst Properties | | |
| Wt. % Co | 2.98 | 3.80 |
| Wt. % Re | 0.21 | 0.20 |
| Density, g/cc | 1.59 | 1.22 |
| Volumetric Co loading, g/100 cc | 4.7 | 4.6 |
| RIM thickness, microns (+/− 40%) | 90 | 80 |
| Catalytic Test (200° C., 280 psig) | | |
| Productivity | 166 | 187 |
| Mol % CH₄ | 7.5 | 6.0 |

These data thus clearly show that titania supports with improved porosity provide superior performance when used to make cobalt hydrocarbon synthesis catalysts. Higher porosity generates better cobalt dispersion, which in turn leads to higher intrinsic hydrocarbon synthesis activity. Higher porosity also benefits forms of the catalyst which are somewhat diffusion limited, such as surface metal coated.

The hydrocarbon synthesis reactions can be considered with these catalysts in fixed bed, or ebullating bed reactors with or without the recycle of any unconverted gas and/or liquid product. The $C_{10}^+$ product that is obtained is an admixture of linear paraffins and olefins which can be further refined and upgraded to high quality middle distillate fuels, or such other products as mogas, diesel fuel, jet fuel and the like. A premium grade middle distillate fuel of carbon number ranging from about $C_{10}$ to about $C_{20}$ can also be produced from the $C_{10}^+$ hydrocarbon product.

It is apparent that various modifications and changes can be made without departing the spirit and scope of the present invention.

What is claimed is:

1. A process for the conversion of synthesis gas to hydrocarbons at high activity which comprises contacting at reaction conditions a feed comprised of an admixture of carbon monoxide and hydrogen, in H₂:CO molar ratio equal to or greater than 0.5:1 at pressure greater than or equal to 80 psig, over a catalyst composition comprised of a catalytically effective amount of a Group VIII non-noble metal catalytically active for the conversion of synthesis gas to hydrocarbons dispersed upon a titania support in which there is incorporated from about 0.1 percent to about 10 percent of an inorganic oxide binder selected from the group consisting of alumina, and zirconia based on the weight of the titania-binder support to provide a titania-binder support having a pore volume ranging from about 0.2 cc/g to about 0.5 cc/g and surface area ranging from about 8 m²/g to about 70 m²/g.

2. The process of claim 1 wherein the Group VIII metal of the catalyst composition is cobalt.

3. The process of claim 1 wherein the Group VIII metal of the catalyst composition is cobalt, and the cobalt is promoted with a metal selected from the group consisting of rhenium, hafnium, zirconium, cerium, thorium, and uranium.

4. The process of claim 1 wherein the titania component of the catalyst support has a rutile:anatase weight ratio of at least about 3:2.

5. The process of claim 4 wherein the titania component of the support has a rutile:anatase weight ratio ranging from about 3:2 to about 100:1, and higher.

6. The process of claim 1 wherein the inorganic oxide binder contained within the titania support component of the catalyst is in concentration ranging from about 0.5 percent to about 10 percent.

7. The process of claim 1 wherein the inorganic oxide binder contained within the titania support component of the catalyst ranges from about 1 percent to about 5 percent.

* * * * *